United States Patent [19]

Jain et al.

[11] Patent Number: 4,505,890
[45] Date of Patent: Mar. 19, 1985

[54] CONTROLLED RELEASE FORMULATION AND METHOD

[75] Inventors: Nemichand B. Jain, Monmouth Junction; Mahendra R. Patel, East Brunswick, both of N.J.

[73] Assignee: E. R. Squibb & Sons, Inc., Princeton, N.J.

[21] Appl. No.: 509,493

[22] Filed: Jun. 30, 1983

[51] Int. Cl.$^3$ .......................... A61K 9/24; A61K 9/22; A61K 9/62

[52] U.S. Cl. ........................................ 424/21; 424/19; 424/35

[58] Field of Search ............... 424/19, 21, 35

[56] References Cited

U.S. PATENT DOCUMENTS

| | | | |
|---|---|---|---|
| 3,065,143 | 4/1960 | Christenson et al. | 167/82 |
| 3,427,378 | 2/1969 | Henderson et al. | 424/14 |
| 3,444,290 | 5/1969 | Wal et al. | 424/4 |
| 3,458,622 | 3/1969 | Hill | 424/19 |
| 3,555,151 | 1/1971 | Kaplan et al. | 424/156 |
| 3,574,820 | 4/1971 | Johnson et al. | 424/32 |
| 3,976,764 | 8/1976 | Watanabe et al. | 424/19 |
| 4,140,755 | 2/1979 | Sheth | 424/21 |
| 4,173,626 | 11/1979 | Dempski et al. | 424/19 |
| 4,248,857 | 2/1981 | DeNeale et al. | 424/21 |
| 4,252,786 | 2/1981 | Weiss et al. | 424/19 |
| 4,259,314 | 3/1981 | Lowey | 424/19 |
| 4,309,404 | 1/1982 | DeNeale et al. | 424/21 |
| 4,309,405 | 1/1982 | Guley et al. | 424/21 |

*Primary Examiner*—Shep K. Rose
*Attorney, Agent, or Firm*—Lawrence S. Levinson; Burton Rodney

[57] ABSTRACT

A controlled release pharmaceutical formulation which undergoes substantially zero order release of active drug is provided, preferably in the form of a coated tablet, containing a core portion from which the angiotensin converting enzyme inhibitor (S)-1-[3-(benzoylthio)-2-methyl-1-oxopropyl]-L-proline is slowly released over a controlled length of time. The core also includes one or more hydrocolloid gelling agents having a viscosity of within the range of from about 8000 to about 100,00 centipoises in 2% solution at 20° C., such as hydroxypropylmethyl cellulose and/or methyl cellulose, one or more inert fillers or excipients, one or more lubricants, and optionally one or more anti-adherents such as silicon dioxide and water. The above-described core is coated with a conventional pharmaceutical coating composition. A method of using such controlled release formulations in treating hypertension is also provided.

9 Claims, No Drawings

CONTROLLED RELEASE FORMULATION AND METHOD

FIELD OF THE INVENTION

The present invention relates to a controlled release formulation, preferably in the form of a tablet, for slowly releasing the angiotensin converting enzyme inhibitor (S)-1-[3-(benzoylthio)-2-methyl-1-oxopropyl]-L-proline.

BACKGROUND OF THE INVENTION

It is of great advantage to both the patient and clinician that medication be formulated so that it may be administered in a single daily dose from which the drug is uniformly released over a desired extended period of time. Until now, this has been accomplished in several different ways. Medicinal agents are either coated with varying thicknesses of a relatively insoluble material or are embedded into a rigid lattice of resinous material. The medicinal agent is continuously made available for absorption into the blood stream to replace the amount eliminated while the dosage form is passing through the gastro-intestinal tract of the patient. However, certain types of medicinal agents are not suited to absorption during passage through the gastro-intestinal tract. For example, most acidic medicinals are principally absorbed from the stomach, whereas most basic medicinals are absorbed primarily from the intestines.

U.S. Pat. No. 3,458,622 to Hill discloses a controlled release tablet for the administration of medicinal agents over a prolonged period of up to about eight hours. This patent discloses a compressed tablet for the prolonged release of a medicament containing that medicament in a core formed from a polymeric vinyl pyrrolidone, preferably polyvinyl pyrrolidone (PVP), and a carboxyvinyl hydrophilic polymer (hydrocolloid) such as those marketed under the trademark Carbopol. The core material formed from the two polymeric substances provides the controlled release effect by forming a complex under the action of water or gastric fluid. This complex is gel-like in consistency and retards the diffusion of active ingredient from the tablet. The controlled release rate of the drug is dependent upon the interaction of the two principal ingredients, the polymer and the hydrocolloid, in the presence of water to form a gummy complex of low solubility. Since little of the gummy complex is present initially, the drug at or near the surface dissolves fairly rapidly and there is an initial surge wherein a relatively large amount of drug is released in the beginning for a period of about one hour. As the colloid complex is formed, once aqueous solution penetrates the surface of the tablet, the gel retards the dissolution of the drug out of the tablet.

U.S. Pat. No. 4,252,786 to Weiss et al recognizes the initial surge problem in the Hill patent and resolves same by applying a rupturable relatively water-insoluble water-permeable film formed of a combination of hydrophobic and hydrophilic polymers over an insoluble swelling type delayed release matrix or core containing the medicament which core includes a blend of polyvinyl pyrrolidone and a carboxyvinyl hydrophilic polymer. Weiss et al in Column 2 states as follows:

"Initially, while the film is intact, the release of the drug contained in the matrix is primarily controlled by diffusion of solvent and solute molecules through the film. As water or gastric fluid permeates through the film, the gummy complex forms and the slight swelling of the complex causes the film to rupture or erode. The release rate is then controlled by the gummy complex. The application of a relatively water insoluble, water permeable film primarily controls the drug release rate while the matrix gel is being generated and a smoother, gradual, more uniform release rate is achieved during the entire period of about eight to twelve hours, approaching a zero order release pattern. The release pattern of the core, upon application of the film, can be varied over a range by varying the composition and amount of film-forming mixture."

U.S. Pat. No. 4,140,755 to Sheth et al discloses a sustained release formulation in the form of sustained release tablets which are hydrodynamically balanced to have a bulk density (specific gravity) of less than 1 in contact with gastric fluid and which will therefore remain floating in gastric fluid which has a specific gravity of between 1.004 and 1.010. The Sheth et al sustained release formulation contains a homogeneous mixture of one or more medicaments with one or more hydrophilic hyrocolloids, such as hydroxypropyl methyl cellulose having a viscosity of 4000 cps. The hydrocolloids when contracted with gastric fluid at body temperatures form a sustained gelatinous mix on the surface of the tablet causing the tablet to enlarge and acquire a bulk density of less than 1. The medicament is slowly released from the surface of the gelatinous mix which remains buoyant in the gastric fluid.

All of the medicament in the tablet disclosed in the Sheth et al patent is released in the stomach.

U.S. Pat. Nos. 4,309,404 and 4,248,857 to Deneale et al disclose slow release formulations for many different drugs and classes of drugs including propranolol and other antihypertensives which formulations are formed of a core material containing the active drug (31–53%), carboxypolymethylene (7–14.5%), zinc oxide (0–3%), stearic acid (4.5 to 10%) and mannitol (3 to 30%); a seal coating surrounding the core; and a sugar coating surrounding the seal coating.

U.S. Pat. No. 4,309,405 to Guley et al discloses a sustained release tablet similar to that disclosed in DeNeale et al (U.S. Pat. No. 4,309,404) except that the core contains 20 to 70% drug, 30 to 72% of a mixture of a water-soluble polymer such as hydroxypropylmethyl cellulose or hydroxypropyl cellulose and water-insoluble polymer (ethylcellulose alone or in admixture with carboxypolymethylene, hyroxypropyl cellulose and the like).

Each of the DeNeale et al and Guley et al patents disclose that their compositions provide substantially zero order release of the core contained drug for about 12 hours following the first hour of administration. Thus, zero order release is only obtained after the initial surge of release of drug in the first hour.

U.S. Pat. No. 4,259,314 to Lowey discloses a controlled long-acting dry pharmaceutical composition which includes a dry carrier formed from a mixture of hydroxypropylmethyl cellulose (viscosity of 50 to 4000 cp in 2% aqueous solution at 20° C.) and hydroxypropyl cellulose (viscosity of 4000 to 6500 cp for a 2% aqueous solution at 25° C.) which dry carrier is employed with a therapeutic agent among which include aspirin, ascorbic acid and nitroglycerin.

U.S. Pat. Nos. 3,065,143 to Christenson et al, 3,147,137 to Playfair, 3,444,290 to Wal et al, 3,427,378 to Henderson et al, 3,555,151 to Kaplan et al, 3,574,820 to Johnson et al, and 3,976,764 to Watanabe and 4,173,626 to Dempski et al disclose various sustained release tablets which include gelling agents none of which include as the active ingredient an angiotensin converting enzyme inhibitor.

DESCRIPTION OF THE INVENTION

In accordance with the present invention, a controlled relese formulation for the time release of medicament, preferably in the form of a tablet, is provided, which is exceptional as a release mechanism for zero order release of the angiotensin converting enzyme inhibitor (S)-1-[3-(benzoylthio)-2-methyl-1-oxopropyl]-L-proline over a period of 8 hours or more substantially starting from ingestion of the tablet. The controlled release formulation of the invention is preferably in the form of a coated tablet which includes a core containing the medicament (S)-1-[3-(benzoyl-thio)-2-methyl-1-oxopropyl]-L-proline, one or more hydrocolloid gelling agents having a viscosity of within the range of from about 8000 to about 100,000 centipoises in 2% aqueous solution at 20° C., one or more fillers or excipients and one or more lubricants, and optionally one or more anti-adherents, water and/or any other conventional additives. The core will be coated with an acceptable pharmaceutical coating which will include one or more film-formers, one or more plasticizers, one or more solvents and other conventional ingredients.

The angiotensin converting enzyme inhibitor (S)-1-[3-(benzoylthio)-2-methyl-1-oxopropyl]-L-proline which has the structure

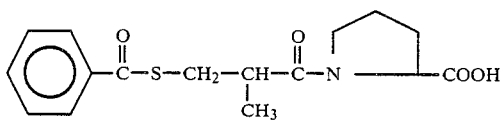

and a method for its preparation are disclosed in U.S. Pat. No. 4,105,776 to Ondetti et al.

Upon oral ingestion of the sustained release tablet of the invention, the tablet coating first slowly peels off leaving the core contents in contact with gastric fluid. Upon contact with gastric fluid, the outermost hydrocolloid particles hydrate and swell to form a gelatinous mass which acts as a protective barrier. Medicament is released by diffusion through the gel layer. In fact, the medicament is released substantially uniformly over a period of 8 hours or more in a zero order release substantially starting from ingestion to provide substantially the same therapeutic efficacy for the drug as provided by the identical dosage of drug administered in divided doses.

The medicament, namely, the angiotensin converting enzyme inhibitor (S)-1-[3-(benzoylthio)-2-methyl-1-oxopropyl]-L-proline, will be present in an amount of at least about 60% by weight of the core and preferably in an amount within the range of from about 15 to about 85% and more preferably, from about 40 to about 75% by weight of the core.

The hydrocolloid, as indicated, is essential to the practice of the invention and will be of the type to provide a viscosity of 8000 to 100,000 centipoises in a 2% aqueous solution at 20° C. and will be present in an amount small enough to ensure that a zero order release is obtained not only after the first hour, but substantially immediately after ingestion. Thus, the hydrocolloid is provided in an amount within the range of from about 8 to about 15% by weight of the core and preferably from about 10 to about 14%. Examples of hydrocolloids suitable for use herein include, but are not limited to, methyl cellulose, hydroxypropyl cellulose, hydroxypropylmethyl cellulose, hydroxyethyl cellulose, and sodium carboxymethyl cellulose. Other examples of suitable hydrocolloids are set out in U.S. Pat. No. 4,140,755 to Sheth et al.

The sustained release tablets will also include additional edible non-toxic ingredients as conventionally employed in solid medicinal dosage forms. Thus, the core of the tablets of the invention will include from about 8 to about 15% by weight and preferably from about 10 to about 14% by weight of one or more excipients such as lactose, sugar, corn starch, modified corn starch, mannitol, sorbitol, inorganic salts such as calcium carbonate or cellulose derivatives such as wood cellulose and microcrystalline cellulose, and one or more tabletting lubricants in an amount within the range of from about 0.5 to about 8% by weight of the core, and preferably from about 1 to about 4% by weight of the core, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

The coating layer which is applied over the core may comprise any conventional coating formulations and will include one or more film-formers or binders, such as a hydrophilic polymer like hydroxypropylmethyl cellulose and a hydrophobic polymer like ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthlate, castor oil and the like.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent composition.

A preferred sustained release tablet in accordance with the present invention will inlucde a core containing from about 40 to about 75% by weight (S)-1-[3-(benzoylthio)-2-methyl-1-oxopropyl]-L-proline, from about 10 to about 14% by weight of the hydrocolloid gelling agent which preferably is methyl cellulose and/or hydroxypropylmethyl cellulose, from about 10 to about 14% by weight of an excipient which preferably is lactose, from about 2 to about 5% by weight of a silica flow agent, and from about 1 to about 4% by weight of one or more tabletting lubricants which preferably is a mixture of magnesium stearate and stearic acid (all of such % being based on the weight of the core) and a coating which contains a film former such as ethyl cellulose, hyroxypropylmethyl cellulose and a plasticizer such as triethyl citrate.

The sustained release tablets of the invention may be prepared as follows. A mixture of the angiotensin converting enzyme inhibitor (S)-1-[3-(benzoylthio)-2-methyl-1-oxopropyl]-L-proline, gelling agent and excipients are thoroughly mixed, for example, using a conventional blender. The above mixture is then wet granulated using an aquoues solution of gelling agent. Thereafter, the tabletting lubricant and silica flow agent, if present, are added and the mixture is thoroughly mixed and then compressed into tablet cores. The coating solution formed of film formers, plasticizers and one or more solvents is then sprayed on the cores to form the tablet of the invention.

PREPARATION OF (S)-1-[3-(BENZOYLTHIO)-2-METHYL-1-OXO-PROPYL]-L-PROLINE

A. Acid Chloride of D(−)-benzoylthioisobutyric acid 54.75 ml (0.75 mole) of $SOCl_2$ was stirred on ice while 56.25 g (0.25 mole) of D(−)-benzoylthioisobutyric acid (Courtesty, Oce Andeno) was added, portionwise over 30 minutes. While stirring, the flask was maintained under house vacuum with chilling for an additional two hours, then allowed to warm to room temperature and stirred under vacuum for two additional hours.

Excess $SOCl_2$ was removed on the rotary evaporator, the last traces removed by stripping off benzene aliquots (3×50 ml) to yield 61 g of green oil.

B. (S)-1-[3-(benzoylthio)-2-methyl-1-oxopropyl]-L-proline

To a mixture of 28.8 g (250 mMol) of L-proline and 52 g (0.62 mole) of $NaHCO_3$ in a well agitated reaction kettle with 220 ml of $H_2O$, was added dropwise over 5 hours, 61 g (250 mMol) of the acid chloride derivative of D(−)-benzylthioisobutyric acid.

During addition, the temperature was maintained between 17°–20° C. and the pH between 7.5–8.0. After the addition was complete, stirring was continued for 30 minutes, then 220 ml $H_2O$ and 150 ml $CH_2Cl_2$ were added. The layers were separated, and the aqueous layer was acidified to pH 2.2 with concentrated HCl and extracted with EtOAc (4×200 ml).

The organic extracts were dried, filtered and stripped to yield 80 g of crude oil which was taken up in 200 ml of xylene, and diluted with 600 ml of hexane. After chilling, solids were collected and dried to yield 70.3 g white crystalline solid (0.218 mole, 87.3%) of title compound.

The above material (2.5 g) was recrystallized from hot xylene (10 ml) to give a colorless product (1.6 g), m.p. 85°–86° d.

Analysis calcd for $C_{16}H_{19}NO_4S$: C, 59.79; H, 5.96; N, 4.36; S, 9.98. Found: C, 59.69; H, 5.94; N, 4.21; S, 10.27.

The following example represents a preferred embodiment of the present invention.

EXAMPLE

A sustained release formulation capable of slowly releasing the angiotensin converting enzyme inhibitor (S)-1-[3-(benzoylthio)-2-methyl-1-oxopropyl]-L-proline for a period of up to 8 hours or more and having the following composition is prepared as described below.

| Ingredient | Amount (mg) |
| --- | --- |
| Core Composition | |
| (S)—1-[3-(benzoylthio)-2-methyl-1-oxopropyl]-L-proline | 150 |
| Hydroxypropyl methyl cellulose (hydrophilic polymer)- 15,000 cp in 2% solution at 20° C.) | 25 |
| Lactose | 23 |
| Silica (glidant) (Syloid 244) | 0.5 |
| Magnesium stearate (lubricant) | 0.5 |
| Stearic acid (lubricant) | 4 |
| Purified water q.s. | |
| Coating Composition | |
| Hydroxypropylmethyl cellulose (hydrophilic polymer) | 7.5 |
| Ethyl cellulose (hydrophobic film former or binder) | 4 |
| Triethyl citrate (plasticizer) | 0.5 |
| Ethyl alcohol (solvent) q.s. | |
| Methylene chloride (solvent) q.s. | |

The q.s. ingredients were for processing purposes only and do not appear in the final product.

The (S)-1-[3-(benzoylthio)-2-methyl-1-oxopropyl]-L-proline, lactose and the hydroxypropyl methyl cellulose are mixed together and then are wet granulated using an aqueous hydroxypropylmethyl cellulose solution. The mixture is passed through a 40 mesh screen and thereafter the silica flow agent, stearic acid and magnesium stearate are added thereto. The so-formed mixture is then thoroughly mixed and compressed into tablet cores.

A coating solution formed of a mixture of hydroxypropylmethyl cellulose, ethyl cellulose and triethyl citrate dissolved in a mixture of ethyl alcohol and methylene chloride is sprayed on the cores to form the sustained release tablets of the invention.

The so-formed sustained release tablet of the invention is found to undergo substantially zero order release so that it slowly and uniformly releases drug over an 8-hour period.

What is claimed is:

1. A controlled release formulation in the form of a tablet from which the angiotensin converting enzyme inhibitor (S)-1-[3-(benzoylthio)-2-methyl-1-oxopropyl]-L-proline is released at a controlled rate, comprising a core and a pharmaceutically acceptable coating therefor, said coating comprising one or more film-formers or binders and one or more plasticizers, and said core comprising from about 15 to about 85% by weight (S)-1-[3-(benzoylthio)-2-methyl-1-oxopropyl]-L-proline, from about 8 to about 14% by weight of one or more hydrocolloid gelling agents having a viscosity of within the range of from about 8000 to about 100,000 centipoises in 2% solution of 20° C., and which is methyl celulose, hydroxypropyl cellulose, hydroxy ethyl cellulose, sodium carboxymethyl cellulose or mixtures thereof, from about 8 to about 15% by weight of one or more excipients, from about 0.5 to about 8% by weight of one or more lubricants, from 0 to about 8% by weight of one or more anti-adherents, and from 0 to about 3% by weight water, all of said % being based on the weight of said core, said tablet adapted to undergo substantially zero order release of (S)-1-[3-(benzoylthio)-2-methyl-1-oxopropyl]-L-proline over an 8 hour or more period.

2. The tablet as defined in claim 1 wherein said core contains (S)-1-[3-(benzoylthio)-2-methyl-1-oxopropyl]-L-proline in an amount within the range of from about 60 to about 85% by weight of said core.

3. The tablet as defined in claim 1 wherein said hydrocolloid is methyl cellulose, hydroxypropyl cellulose, hydroxypropylmethyl cellulose or a mixture of two or more of such cellulose derivatives.

4. The tablet as defined in claim 1 wherein said excipient is lactose, sugar, corn starch, modified corn starch, mannitol, sorbitol, inorganic salts or cellulose.

5. The tablet as defined in claim 3 wherein the excipient is lactose and the lubricant is magnesium stearate, stearic acid or a mixture thereof.

6. The tablet as defined in claim 1 wherein the coating includes one or more film formers and/or plasticizers.

7. The tablet as defined in claim 1 wherein the excipient is lactose, the lubricant is a mixture of magnesium stearate and stearic acid, the gelling agent includes methyl cellulose and hydroxypropylmethyl cellulose, and further including silica as an anti-adherent.

8. The tablet as defined in claim 6 wherein the coating includes hydroxypropylmethyl cellulose and ethyl cellulose as a film former and triethyl citrate as a plasticizer.

9. A method of alleviating hypertension in a mammalian specie which comprises administering the sustained release tablet as defined in claim 1 containing an effective amount of the angiotensin converting enzyme inhibitor (S)-1-[3-(benzoylthio)-2-methyl-1-oxopropyl]-L-proline.

* * * * *